United States Patent
Brunnhofer

(10) Patent No.: US 10,447,256 B2
(45) Date of Patent: Oct. 15, 2019

(54) METHOD AND DEVICE FOR DETECTING SIGNAL PULSES

(71) Applicant: AVL LIST GmbH, Graz (AT)

(72) Inventor: Georg Brunnhofer, Graz (AT)

(73) Assignee: AVL LIST GmbH, Graz (AT)

(*) Notice: Subject to any disclaimer, the term of this patent is extended or adjusted under 35 U.S.C. 154(b) by 0 days.

(21) Appl. No.: 15/749,699

(22) PCT Filed: Aug. 12, 2016

(86) PCT No.: PCT/EP2016/069193
§ 371 (c)(1),
(2) Date: Feb. 1, 2018

(87) PCT Pub. No.: WO2017/025619
PCT Pub. Date: Feb. 16, 2017

(65) Prior Publication Data
US 2018/0226958 A1    Aug. 9, 2018

(30) Foreign Application Priority Data
Aug. 12, 2015 (AU) .................. 50716/2015

(51) Int. Cl.
*H03K 5/1534* (2006.01)
*G01T 1/17* (2006.01)
*G01T 1/172* (2006.01)
*G01N 15/06* (2006.01)
*G01R 19/00* (2006.01)
*G01N 15/00* (2006.01)

(52) U.S. Cl.
CPC ........ *H03K 5/1534* (2013.01); *G01N 15/065* (2013.01); *G01T 1/17* (2013.01); *G01T 1/172* (2013.01); *G01N 2015/0046* (2013.01); *G01R 19/0053* (2013.01)

(58) Field of Classification Search
CPC .................................................. H03K 5/1534
See application file for complete search history.

(56) References Cited

U.S. PATENT DOCUMENTS 4,803,701 A    2/1989  Rhodes
4,837,437 A *  6/1989  Forster .................. G01T 1/172
                                                     250/336.1

(Continued)

FOREIGN PATENT DOCUMENTS

DE    3635477 A1    4/1988
JP    H05149866 A   6/1993

(Continued)

OTHER PUBLICATIONS

Austrian Search Report Application No. A50716/2015 Completed Date: Jun. 27, 2017 1 page.

(Continued)

*Primary Examiner* — Hai L Nguyen
(74) *Attorney, Agent, or Firm* — Whitmyer IP Group LLC

(57) ABSTRACT

A device for detecting signal pulses in an analog measurement signal of a particle counter is disclosed. The device includes an AD converter and an evaluation unit, wherein the evaluation unit includes a slope evaluation unit, which determines signal pulses by evaluating the pulses between adjacent samples in the digital data stream of the AD converter in real time.

14 Claims, 2 Drawing Sheets

(56) References Cited

U.S. PATENT DOCUMENTS 9,494,676 B2 * 11/2016 Griessbaum .......... G01F 23/284
2003/0099172 A1 5/2003 Park et al.
2012/0126771 A1 5/2012 Tuten

FOREIGN PATENT DOCUMENTS

| KR | 20030049008 A | 6/2003 |
| KR | 20030052796 A | 6/2003 |
| WO | 9322692 A1 | 11/1993 |
| WO | 2007065179 A1 | 6/2007 |

OTHER PUBLICATIONS

International Search Report & Written Opinion of the International Searching Authority Application No. PCT/EP2016/069193 Completed Date: Nov. 3, 2016; dated Nov. 17, 2016 12 pages.
International Preliminary Report on Patentability Application No. PCT/EP2016/069193 dated Feb. 13, 2018 8 pages.

* cited by examiner

METHOD AND DEVICE FOR DETECTING SIGNAL PULSES

TECHNICAL FIELD

The present teachings relate to a device for detecting signal pulses in an analogue measurement signal of a particle counter, wherein the device has an AD converter and an evaluation unit. Further, the present teachings relate to the use of this device and a method for detecting signal pulses in an analogue measurement signal having such a device.

BACKGROUND

Particle counters generally have a carpet of light, through which a mostly individualised particle stream is passed, each particle generating stray light as it passes, which is detected by a light sensor. In order to improve measurability, the particles usually first pass through a condensation unit, in which condensation droplets grow on particles. Due to the greater size and the uniformity of the condensation droplets, counting is enabled as opposed to a direct measurement of the particles.

Due to the Gaussian distribution of light intensity of the carpet of light, a passing particle generates an equally Gaussian signal pulse. In an optimal case, each individual particle provides a single stray light pulse, which corresponds to a temporal profile of sporadically occurring signal pulses. The statistic probability distribution of discrete events may here be determined via a Poisson distribution.

If the temporal distance between particles is too small, coincidence will occur, wherein the signal pulses generated by the particles following one another in quick succession superimpose to form a single signal pulse and can no longer be separated as two individual events.

The light sensor generates an analogue measurement signal that is evaluated for detecting and counting the signal pulses. Usually, a threshold value is defined here, wherein the generated signal pulse of a passing particle is detected by a comparator member and the particle is regarded as having been detected when this threshold value is exceeded. In a case where a threshold value is selected to be too high it may occur that signal pulses that are too small are falsely not counted. However, if the threshold value is selected to be too low, then signal pulses that are too close together and partially overlap (coincidences) are detected only as one single signal pulse, and therefore some signal pulses are not detected. Also background noise may lead to false results in the case of too low a threshold value.

What is particularly disadvantageous is if the measured pulse ensemble has such a drift behaviour that said ensemble, during the measurement, moves out of the measurement range defined by the threshold value. Signal evaluation via threshold values may here unnoticeably lead to a wrong result.

Usually, signal evaluation is carried out in the analogue domain because the signal pulses in the measurement signal are very short, usually in a range of 80 to 200 ns, so that digitalisation requires a very high sampling rate. Although AD converters are available that allow a sufficiently high sampling rate even for very small signal pulses, evaluation by means of threshold values in the digital domain has however no substantial advantages over the analogue domain, so that in general evaluation in the analogue domain provides for a simpler and therefore more preferred solution.

Thus, there is a need in the prior art for devices and methods for detecting signal pulses, which allow an improved detection of coincidences and an enhanced counting accuracy and which provide a possibility of detecting, evaluating and compensating for a drift behaviour of the measurement signal.

SUMMARY

According to the present teachings, these and other objects of the prior art are achieved by means of a device of the type mentioned in the beginning, wherein the evaluation unit has a slope evaluation unit that detects signal pulses by evaluating the slopes between adjacent samples in the digital data stream of the AD converter in real time. In other words, the present teachings allow to provide a device and a method for detecting and counting partially overlapping signal pulses in an analogue measurement signal of a particle counter. Instead of fixed threshold values, the profile of the measurement signal can therefore be evaluated in a simple manner. Slope changes can be evaluated in order to detect pulse peaks. This also allows a drift behaviour to be detected and compensated. An evaluation in real time is required in the case of continuous measurement methods and can be achieved by means of the device according to the present teachings.

In an advantageous embodiment, the AD converter generates the digital data stream at a sampling rate of more than 50 msps (million samples per second or mega samples per second), preferably between 50 and 105 msps. This already allows a detection of signal pulses in the nanosecond range.

Preferably, the detection of signal pulses may be implemented in an integrated circuit, preferably a field programmable gate array. This allows an implementation of the detection algorithms that is close to hardware and yet flexible, and in this way allows a signal evaluation in real time in a simple manner.

In a further advantageous embodiment, the evaluation unit may have a detection unit that detects a signal pulse if a sequence of samples meets the conditions of a parameter set, which parameter set comprises at least one parameter selected from a minimum edge increase, a minimum increase duration and/or a minimum edge decrease. Such a parameter set allows a rapid detection of signal pulses using simple comparative computation operations. No integrators or differentiators are required here.

In order to filter out background noise, the evaluation unit may advantageously comprise a threshold unit that excludes the samples from the evaluation if the samples fall below a predefined detection threshold.

In a further embodiment, the evaluation unit may have a drift detection unit that determines and evaluates the criteria for detecting and/or evaluating the drift behaviour of the measured pulse ensemble. As a result, error sources may be detected early and any deficiencies may be avoided.

Preferably, the criteria for detecting and/or evaluating the drift behaviour may comprise a change in the background light, an average signal pulse amplitude and/or an average signal pulse duration. Such criteria allow a qualified statement to be made in relation to the causes of an occurring drift behaviour, so that corresponding maintenance measures may be scheduled in good time.

Advantageously, the device may have compensation means for compensating a drift behaviour in the particle counter, wherein a control variable of the compensation means is transferred to the evaluation unit for detecting and/or evaluating the drift behaviour of the measurement signal. In particular, a change in the background light of the measuring cell may be compensated using the compensation means, wherein the compensation means may be provided in the analogue domain or in the digital domain. The compensation of the drift behaviour ensures that the zero line of the measurement signal is not displaced. As a result, for example the effectivity of the detection threshold for filtering out background noise is ensured. At the same time, the control variable is used by the evaluation unit as one of the characteristics for the detection and/or evaluation of drift behaviour.

All of the elements of the device, in particular the AD converter, the evaluation unit, the slope evaluation unit, the detection unit, the threshold unit, the drift detection unit and/or the compensation means, as well as all the other functional elements of the device, may be designed, as required, in each case as a separate hardware unit, they may be combined in any desired way to hardware units in subgroups, they may in each case be integrated in different units or they may partially or entirely be implemented as software.

The device may advantageously be used to determine a maintenance time on the basis of a drift behaviour. Here, on the basis of the respective criteria, also specific statements in respect of the type of the required maintenance may be derived.

The method for detecting signal pulses in an analogue measurement signal as mentioned in the beginning provides for signal pulses to be determined by evaluating the slopes between adjacent samples in the digital stream of the AD converter in real time.

Advantageously, the method can detect a signal pulse if a sequence of samples meets the conditions of a parameter set, wherein the parameter set comprises at least one parameter selected from a minimum edge increase (min_incr), a minimum increase duration (peak_valid) and/or a minimum edge decrease (min_decr).

If necessary, also a plurality of different parameter sets may be evaluated and compared in parallel, for example for a dynamic determination of the optimum parameter set with regard to counting accuracy, for categorisation of particle properties or for determining coincidences. The parallel parameter sets may for example also be used for an automatic correction.

Advantageously, samples are evaluated only if they exceed a predefined detection threshold, in order to filter out background noise.

In a preferred embodiment of the method according to the present teachings, criteria for detection and/or evaluation of the drift behaviour of the measured pulse ensemble may be determined, wherein the criteria for detecting and/or evaluating the drift behaviour preferably comprise a change to the background light, an average signal pulse amplitude and/or an average signal pulse duration.

Advantageously, the minimum ratio between the average signal pulse duration and the sampling interval may be less than 40, preferably less than 20 and in particular less than 6. Due to the stable evaluation algorithm, signal pulses may also be reliably detected using just a few samples. This also increases the maximum admissible pass-through rate of the particles. The method according to the present teachings may also be used to detect for example a sampling frequency of 100 msps signal pulses of just 30 ns duration. This corresponds to a ratio between the signal pulse duration ($3*10^8$ s) and the sampling interval ($1*10^{-8}$ s) of 3. For a sufficient and meaningful evaluation of the drift behaviour by the average signal pulse amplitude or the average signal pulse duration, a higher sampling frequency may be useful.

For the detection of partially overlapping signal pulses, deviations from the ideal signal shape may be quantified and subsequently taken into account. The extent of the deviation from the ideal signal shape allows conclusions in respect of occurring coincidences to be made.

BRIEF DESCRIPTION OF THE DRAWINGS

The subject will be explained in more detail below with reference to FIGS. 1 to 3 which show, by way of example, schematically and in a non-limiting way, advantageous embodiments, wherein.

DETAILED DESCRIPTION

Figure 1:
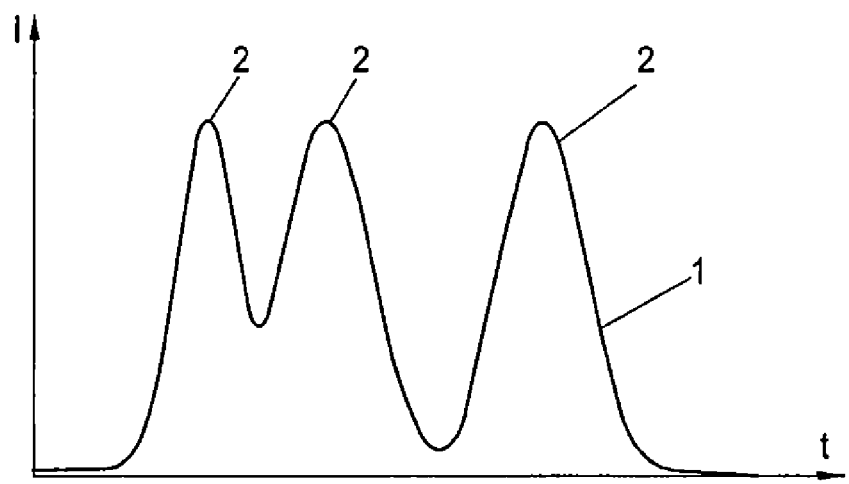
FIG. 1 shows an analogue measurement signal having a plurality of signal pulses.

FIG. 1 shows the profile of a measurement signal 1 recorded by a photodetector, wherein the light intensity I is recorded over the time t. The measurement signal may for example originate from a sensor cell of a condensation particle counter, wherein each of the three signal pulses 2 shown in the measurement signal 1 was generated by a particle passing through the carpet of light of the measurement cell. If the particle, or the aerosol droplet condensated onto the particle, passes through a carpet of light, the light scattered on the particle will impinge onto the photodetector 3 (see FIG. 2) and generate a signal pulse 2. In FIG. 1, the first two signal pulses 2 show a beginning superimposition as may occur in the case of a very quick temporal succession.

The duration of such signal pulses, determined by the particle (end) size and the width of the carpet of light, typically in a range of a few nanoseconds, is for example in a range of 80 to 200 ns.

The level of the signal pulse is associated with the stray light intensity and thus with the particle size. The pulse width allows a conclusion to be made in respect of the period of time the particle needs to pass through the light curtain or the optical detection unit.

Figure 2:
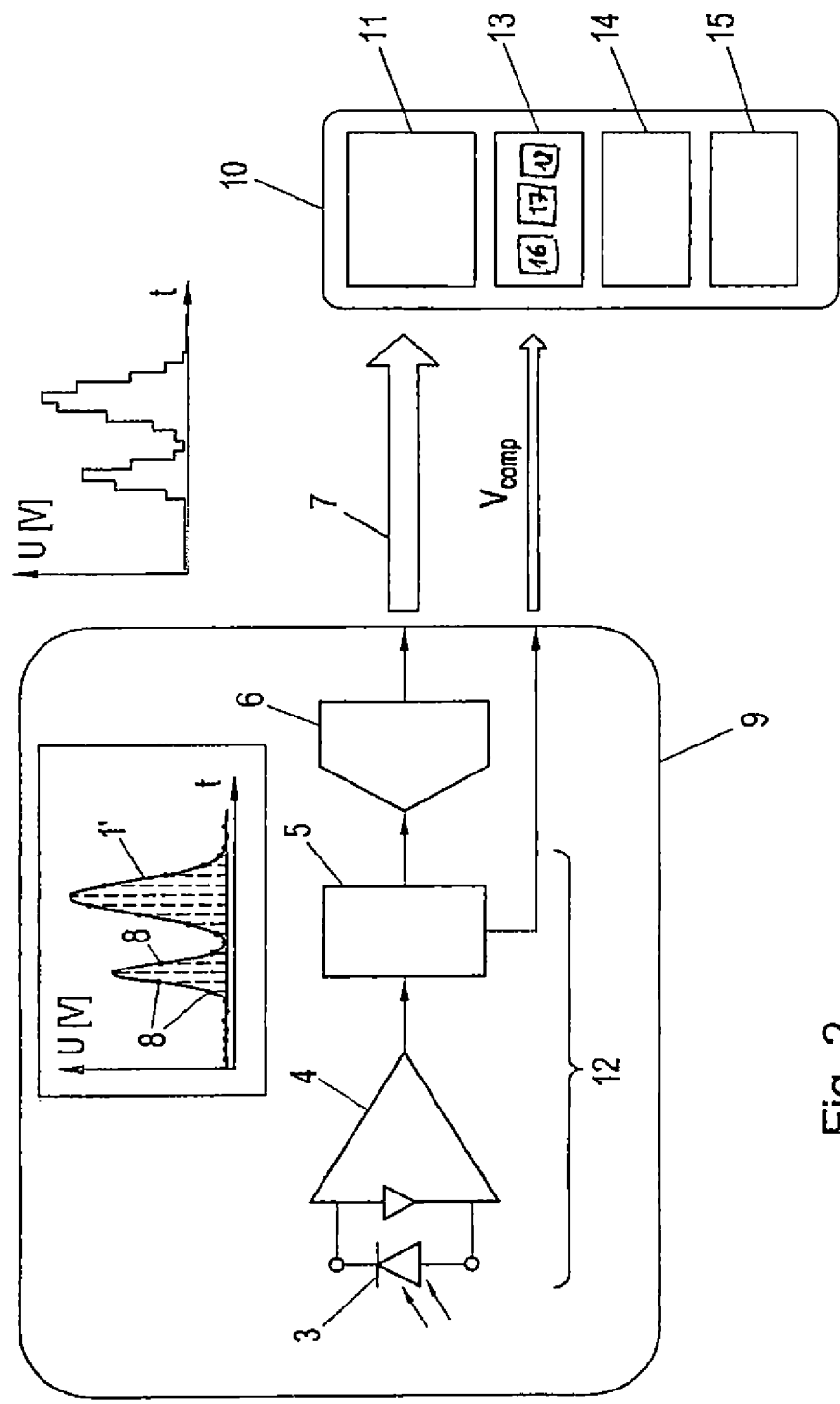
FIG. 2 shows a block diagram of a device for detecting signal pulses using a detector unit and an evaluation unit.

FIG. 2 shows an embodiment example of a device according to the present teachings. The device has a detector unit 9 with a photodetector 3, a transimpedance amplifier 4, a compensation means 5 and an AD converter 6, and an evaluation unit 10 with a field programmable gate array 11.

The current (i.e. the measurement signal 1) generated by the photodetector 3 is amplified using the transimpedance amplifier 4 and is converted in the course of this into a voltage signal 1', before it is digitised by the AD converter. The voltage signal 1' is shown in FIG. 2 in a diagram above the compensation means 5, wherein the samples 8 for digitisation are schematically shown. The voltage signal may be subjected to anti-alias filtering prior to the AD conversion in a known manner.

The small duration of the signal pulse within the nanosecond range requires, during digitisation of the signal, a very high sampling rate, a fast digital signal evaluation algorithm and a correspondingly high bandwidth of the analogue signal path. To this end, for example a high speed photodetector with a high bandwidth may be used as the photodetector 3. Matched to this, the downstream transimpedance amplifier 4 has to have a significantly high gain. In this context it has to be made sure that in the case of a sufficiently high gain bandwidth product, the equally necessary signal bandwidth is ensured (the higher the gain of an amplifier, the more limited its bandwidth will be).

The compensation means 5 compensates for background light fluctuations in the detection chamber. The control variable $V_{comp}$ as used by the compensation means 5 is then forwarded to the evaluation unit 10 and is used as one of several criteria for drift detection. With increasing change in the background light, a conclusion can be made in respect of contamination or decalibration of the measurement system. Drift detection will be described in more detail below.

The signal line from the transimpedance amplifier 4 or the compensation means 5 to the AD converter 6 may preferably be designed via a differential line pair that additionally provides for signal integrity compared to electromagnetic coupling.

The sampling frequency may preferably be in a range of 50 MHz to 105 MHz in order to ensure a sufficiently high resolution of the signal pulses for the subsequent signal evaluation.

The digitised signal is forwarded to the evaluation unit 10 as a digital data stream 7. Since the particle count is based on a continuous detection of signal pulses, the latter have to be detected and evaluated in real time by the evaluation unit 10. The main requirements for the evaluation unit 10 are therefore above all fast data acquisition and consequently the ensurance of the real-time capability of the evaluation algorithm. Both the reading in of the samples of the AD converter at a sampling rate $f_s$ of 50 msps to 105 msps and the detection and evaluation of the stray light pulses are therefore processed in a field programmable gate array (FPGA) 11.

The functions carried out by the evaluation unit 10 may comprise a signal pulse detection and evaluation unit 13, a counting algorithm 14 and a drift detection unit 15 for drift detection and evaluation. These function units may be implemented either directly in the FPGA 11 or in a unit downstream thereto. If necessary, the evaluation unit 10 may also be implemented in a different way (for example without an FPGA), as long as the selected means ensure a sufficient processing speed. The signal pulse detection and evaluation unit 13 further includes a slope evaluation unit 16 for evaluating the slopes between adjacent samples, a detection unit 17 for detecting signal pulses on the basis of parameter sets and a threshold unit 18. The threshold unit 18 ensures that samples are evaluated only if a predefined detection threshold is exceeded.

Due to the requirement of rapid processing and real-time capability of the evaluation algorithm, the mathematic complexity has to be kept low. In order to detect signal pulses and to be able to separate them from each other, the FPGA 11 may evaluate various parameters or conditions associated with these parameters and in this way generate an output signal (or a plurality of output signals), which may then be processed for counting and for further evaluation.

Figure 3:
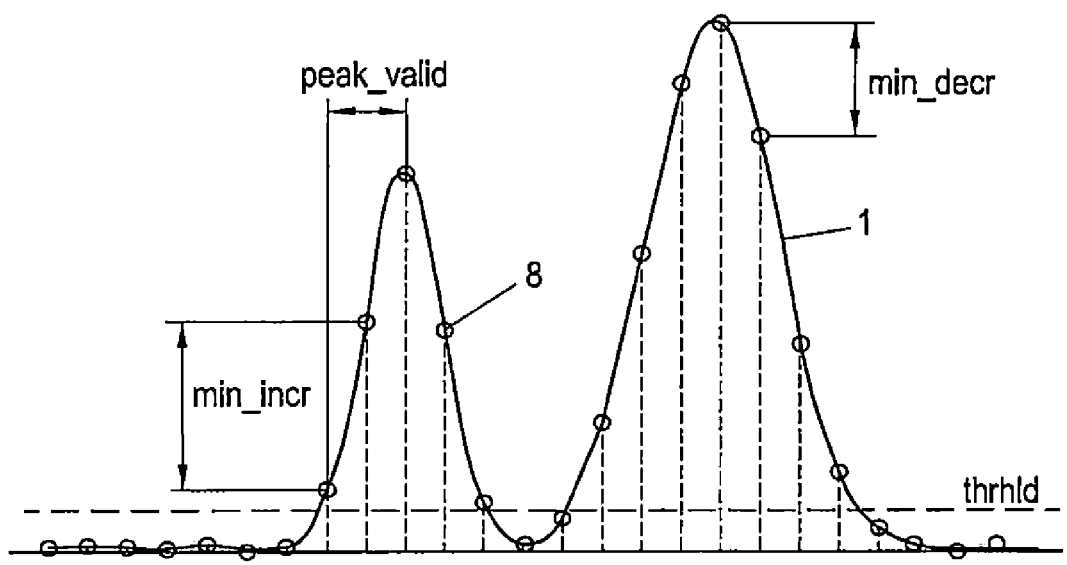
FIG. 3 shows a diagram of digitised signal pulse ensembles for explaining the parameters for the evaluation algorithm.

In FIG. 3, a number of parameters are shown by way of example using a digital measurement signal 1:

1. Detection Threshold (thrhld)

In order to suppress the noise portion of the digital signal evaluation system, the detection threshold is introduced as a threshold value, above which the detection of the signal pulse commences. The condition fixed by the detection threshold can be determined for each individual sample without taking into consideration any adjacent samples. It is to be noted that the detection threshold differs in its function from a threshold value as used in the prior art for generating a counting result, because the detection threshold is not used as the exclusive criterion for particle counting.

2. Minimum Edge Increase (min_incr)

As a characteristic for the increase of a signal pulse and thus also for the frequency thereof, a parameter is used that fixes the minimum signal increase between two successive data points. As soon as the slope between consecutive samples is above the minimum signal increase, the first condition for detecting a signal pulse has been met. For evaluating this parameter (or the condition associated therewith), the determination of the slope between two samples is required. By means of an individual value of a sample, no statement can be made in respect of this parameter.

3. Minimum Increase Duration (peak_valid)

Apart from the value of the slope, also the amplitude of a signal pulse is relevant for a correct detection of the signal pulse. The parameter of the minimum increase duration defines a minimum number of continuously increasing data points a signal profile has to have so as to be detected as a signal pulse. In combination, the conditions checked on the basis of the parameters of the minimum edge increase (min_incr) and the minimum increase duration (peak_valid) are also used as the low-pass filter. In the course of this, any signal peaks that may occur as a result of superimposed noise are filtered out.

4. Minimum Edge Decrease (min_decr)

In order to detect a signal pulse correctly, it further has to be determined whether it has reached a value peak. A value peak is achieved when an increase is followed by a decrease which then falls below the value for a minimum edge decrease. The minimum edge decrease (min_decr) thus constitutes the counterpiece to the minimum edge increase (min_incr). This parameter (or this subcondition) is of particular importance in the separation of signal pulses that follow each other in close temporal succession or which partially overlap each other.

On the basis of the parameters, a parameter set is compiled that has to be met as the condition for the detection of a signal pulse. In order to find the optimum parameter set, a compromise has to be found between counting accuracy, speed of evaluation and noise sensitivity. A simple parameter set would be 1×min_incr+1×min_decr. This would allow signal pulse detection within just three samples.

Also a combination of the parameters min_inc and peak_valid would be possible as a minimum condition. If the parameters min_inc and peak_valid are selected to be sufficiently high, the noise carpet would be suppressed and any relevant signal pulses correctly detected, provided they are not too noisy. If also the parameter min_decr is taken into account, an additional low-pass filter function results.

A parameter set that involves all of the above parameters for detecting signal pulses, could therefore define a sequence of sample values above the detection threshold as a condition for the detection, where the minimum edge increase is exceeded at least once in a constant sequence of slopes, the number of slopes exceeds the minimum increase duration, and where after the maximum value, at least one (negative) slope falls below the minimum edge decrease. Further, it could be defined in which period of time this value has to fall below this edge decrease.

By means of the slope values, also further parameters may be defined (for example a minimum duration for the edge decrease, analogously to the value peak_valid), which are composed to form a parameter set for evaluating the signal.

If necessary, it would also be possible to evaluate a plurality of parameter sets in parallel in order to determine correction factors, for example for detecting coincidences.

Further, the method allows a simple detection and evaluation of the drift behaviour of the measurement device. The drift behaviour may be evaluated on the basis of a plurality of criteria that include the change to the background light $V_{comp}$, the average signal pulse amplitude $A_{peak}$ and the average signal pulse duration $T_{peak}$.

A change to the background light $V_{comp}$ may indicate a de-calibration of the detector unit and/or of the light source. In the course of this, the background light is an important parameter for determining maintenance intervals. The background light may be monitored for example via the control parameter of the compensation means 5.

The average signal pulse amplitude $A_{peak}$ affected in particular is by the particle size. In condensation particle counters, particles grow to a certain and constant size before they pass through the optical detection unit (i.e. the measuring cell of the measurement device). Whilst the beam shape of the carpet of light and variations of the stray angle may lead to deviations of the individual stray light pulses, however the particles image stray light pulses onto the photodetector on average with approximately constant intensity. From the viewpoint of the signal, this means an on average constant pulse amplitude. Therefore, changes in the stray light intensity allow conclusions to be made in respect of a degrading growth quality of the resource in the condenser.

The average signal pulse duration $T_{peak}$ is a measure for the dwell duration of the particle in the carpet of light. A prolonged average signal pulse duration $T_{peak}$ indicates particles that dwell in the carpet of light for a longer period of time, which is an indicator of contamination of the measurement chamber or a change to the resource flow or a change to the carpet of light. The evaluation of this value is essential for the determination of maintenance intervals.

The invention claimed is:

1. A device for detecting signal pulses in an analogue measurement signal of a particle counter,
   wherein the device comprises an AD converter and an evaluation unit,
   wherein the evaluation unit includes a slope evaluation unit, which determines the signal pulses by evaluating the slopes between adjacent samples in the digital data stream of the AD converter in real time,
   wherein the evaluation unit includes a detection unit that detects a signal pulse if a sequence of samples meets the conditions of a parameter set,
   wherein the parameter set includes at least one parameter selected from minimum edge increase, minimal increase duration and/or minimal edge decrease.

2. The device according to claim 1, wherein the AD converter generates the digital data stream at a sampling rate of more than 50 msps.

3. The device according to claim 1, wherein the evaluation unit includes a threshold unit that excludes samples that fall below a predefined detection threshold from the evaluation.

4. The device according to claim 1, wherein the AD converter generates the digital data stream at a sampling rate in a range between 50 and 105 msps.

5. A device for detecting signal pulses in an analogue measurement signal of a particle counter,
   wherein the device comprises an AD converter and an evaluation unit,
   wherein the evaluation unit includes a slope evaluation unit, which determines the signal pulses by evaluating the slopes between adjacent samples in the digital data stream of the AD converter in real time,
   wherein the evaluation unit includes a drift detection unit that determines and evaluates the criteria for detecting and/or evaluating the drift behaviour of the measurement signal.

6. The device according to claim 5, wherein the criteria for detecting and/or evaluating the drift behaviour include a change in the background light, an average signal pulse amplitude and/or an average signal pulse duration.

7. The device according to claim 5,
   wherein the device includes a compensator for compensating a drift behaviour in the particle counter,
   wherein a control variable of the compensator is transferred to the evaluation unit for detecting and/or evaluating the drift behaviour of the measurement signal.

8. A method for detecting signal pulses in an analogue measurement signal using
   a device for detecting signal pulses in an analogue measurement signal of a particle counter,
   wherein the device comprises an AD converter and an evaluation unit,
   wherein the evaluation unit includes a slope evaluation unit, which determines the signal pulses by evaluating the slopes between adjacent samples in the digital data stream of the AD converter in real time,
   wherein a signal pulse is detected if a sequence of samples meets the conditions of a parameter set,
   wherein the parameter set includes at least one parameter selected from a minimal edge increase, a minimal increase duration and/or a minimum edge decrease.

9. The method according to claim 8, wherein samples are evaluated only if they exceed a predefined detection threshold.

10. The method according to claim 8, wherein a minimum ratio between an average signal pulse duration of the signal pulses and a sampling interval of the adjacent samples is less than 40.

11. The method according to claim 8, wherein for detection of partially overlapping signal pulses, deviations from an ideal signal shape are quantified and subsequently taken into account.

12. The method according to claim 8, wherein a minimum ratio between an average signal pulse duration of the signal pulses and a sampling interval of the adjacent samples is less than 20.

13. The method according to claim 9, wherein a minimum ratio between an average signal pulse duration of the signal pulses and a sampling interval of the adjacent samples is less than 6.

14. A method for detecting signal pulses in an analogue measurement signal using
   a device for detecting signal pulses in an analogue measurement signal of a particle counter,
   wherein the device comprises an AD converter and an evaluation unit,
   wherein the evaluation unit includes a slope evaluation unit, which determines the signal pulses by evaluating the slopes between adjacent samples in the digital data stream of the AD converter in real time,
   wherein the criteria for detecting and/or evaluating the drift behaviour of the measured pulse ensemble are determined,
   wherein the criteria for detecting and/or evaluating the drift behaviour include a change in the background light, an average signal pulse amplitude and/or an average signal pulse duration.

* * * * *